United States Patent
Secrest et al.

[11] Patent Number: 5,906,621
[45] Date of Patent: May 25, 1999

[54] ENDOSCOPIC SURGICAL DEVICE

[75] Inventors: Dean J. Secrest, Concord; Marlin E. Younker, Watte Hill, both of Ohio

[73] Assignee: United States Endoscopy Group, Inc., Mentor, Ohio

[21] Appl. No.: 08/649,893

[22] Filed: May 14, 1996

[51] Int. Cl.$^6$ .............................. A61B 17/24; A61B 17/22
[52] U.S. Cl. ......................... 606/114; 606/110; 606/113; 606/127
[58] Field of Search ...................................... 606/106, 110, 606/113, 114, 127, 128, 151, 157, 159, 167; 600/37

[56] References Cited

U.S. PATENT DOCUMENTS

| | | |
|---|---|---|
| 30,471 | 10/1860 | Dudley . |
| 1,609,014 | 11/1926 | Dowd . |
| 1,615,494 | 1/1927 | Waring . |
| 1,931,740 | 10/1933 | Ryan . |
| 2,043,782 | 6/1936 | Sprosty . |
| 2,115,298 | 4/1938 | Brown . |
| 3,244,169 | 4/1966 | Baxter . |
| 3,472,230 | 10/1969 | Fogarty . |
| 3,834,392 | 9/1974 | Lampman et al. . |
| 3,908,661 | 9/1975 | Kramer . |
| 3,920,179 | 11/1975 | Hall . |
| 4,112,932 | 9/1978 | Chiulli . |
| 4,217,890 | 8/1980 | Owens . |
| 4,295,464 | 10/1981 | Shihata . |
| 4,428,375 | 1/1984 | Ellman . |
| 4,447,227 | 5/1984 | Kotsanis . |
| 4,557,255 | 12/1985 | Goodman . |
| 4,619,260 | 10/1986 | Magill et al. . |
| 4,638,802 | 1/1987 | Okada . |
| 4,785,826 | 11/1988 | Ward . |
| 4,790,812 | 12/1988 | Hawkins, Jr. et al. . |
| 4,798,213 | 1/1989 | Doppelt . |
| 4,865,017 | 9/1989 | Shinozuka . |
| 4,905,691 | 3/1990 | Rydell . |
| 4,927,426 | 5/1990 | Dretler . |
| 4,991,593 | 2/1991 | LeVahn . |
| 4,997,435 | 3/1991 | Demeter . |
| 5,018,877 | 5/1991 | Kantz . |
| 5,026,371 | 6/1991 | Rydell et al. . |
| 5,037,379 | 8/1991 | Clayman et al. . |
| 5,074,867 | 12/1991 | Wilk . |
| 5,084,054 | 1/1992 | Bencini et al. . |
| 5,163,942 | 11/1992 | Rydell . |
| 5,190,542 | 3/1993 | Nakao et al. ............................ 606/114 |
| 5,190,555 | 3/1993 | Wetter et al. . |
| 5,201,740 | 4/1993 | Nakao et al. . |
| 5,215,521 | 6/1993 | Cochran et al. . |
| 5,486,182 | 1/1996 | Nakao et al. ............................ 606/114 |
| 5,486,183 | 1/1996 | Middleman et al. .................... 606/113 |

FOREIGN PATENT DOCUMENTS

| | | |
|---|---|---|
| 25796 | 1/1884 | Brazil . |
| 3522-649 | 1/1986 | Germany . |
| 3913-935 | 10/1990 | Germany . |

*Primary Examiner*—Glenn K. Dawson
*Attorney, Agent, or Firm*—Watts Hoffmann Fisher & Heinke

[57] ABSTRACT

An endoscopic surgical device for severing tissue within a subject and for retrieving severed tissue from within the subject is disclosed. The device has a support unit, a tissue severing snare system, and a tissue retrieving net system. The snare and net systems are carried by the support unit and may be inserted into the subject through an orifice or small incision and individually operated to sever and retrieve tissue. The snare system includes a snare, a snare actuator, and a snare deployment and retrieval assembly for transmitting motion between the actuator and the snare. The net system includes a net, a net actuator, a net deployment and retrieval assembly for transmitting motion between the net and its actuator and a net controller for assuring the net is fully opened when deployed.

5 Claims, 4 Drawing Sheets

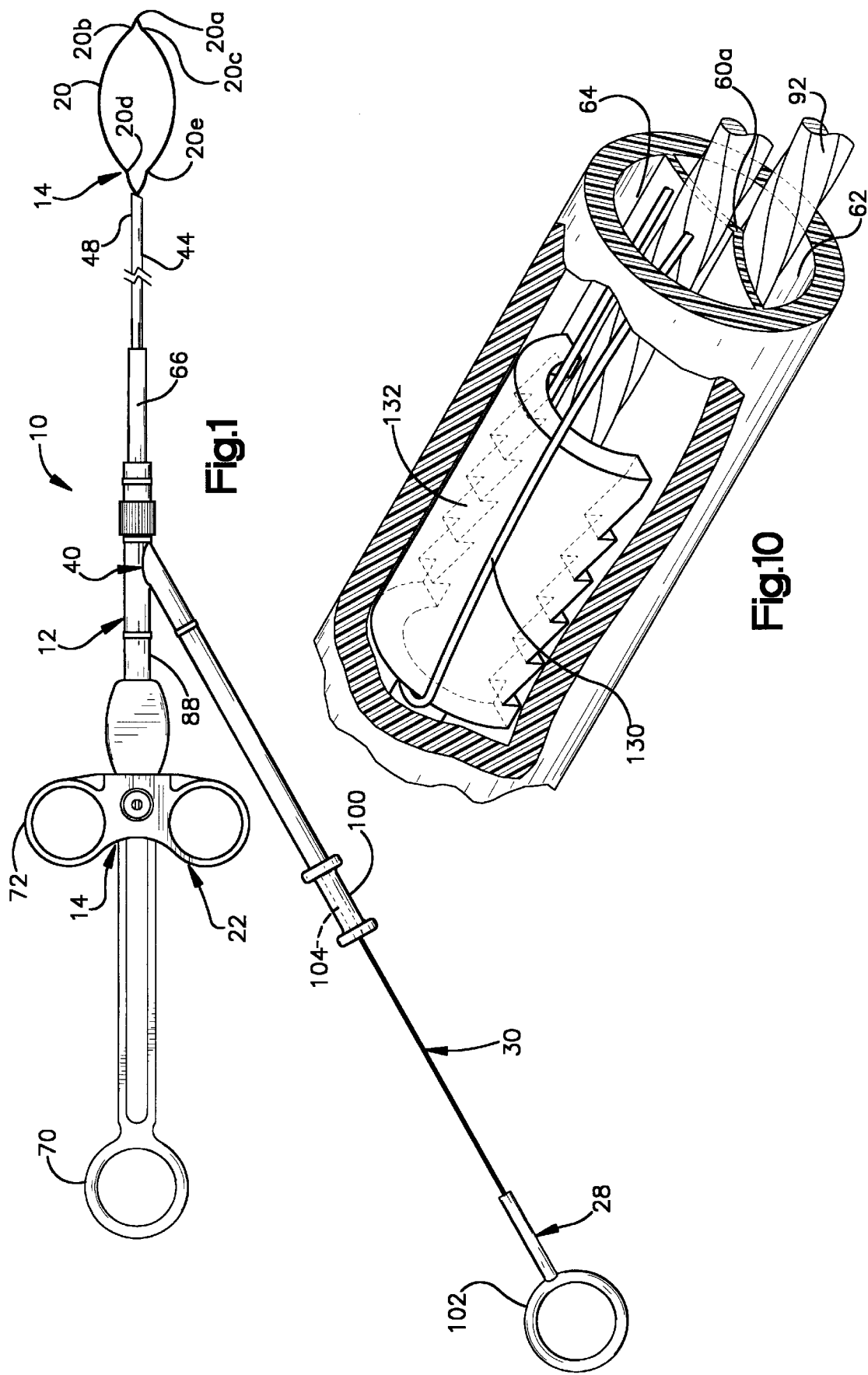

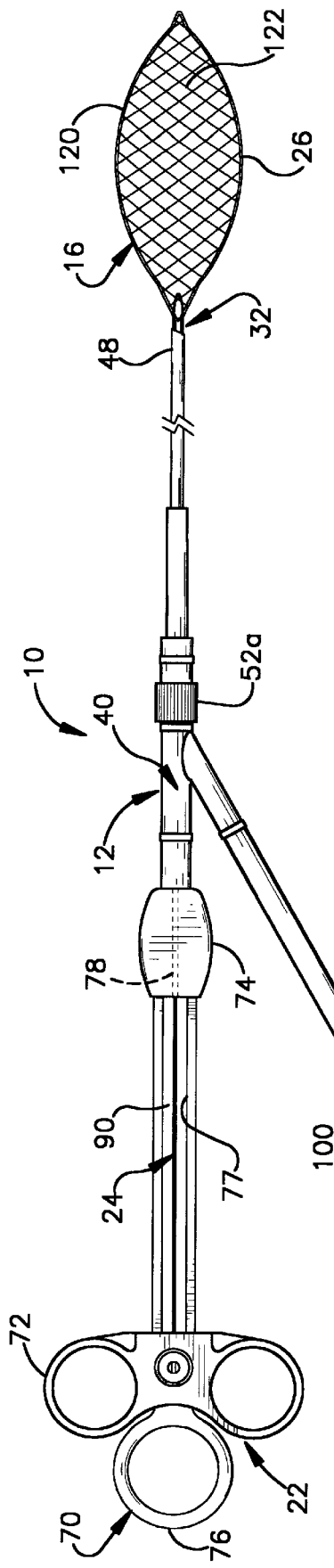

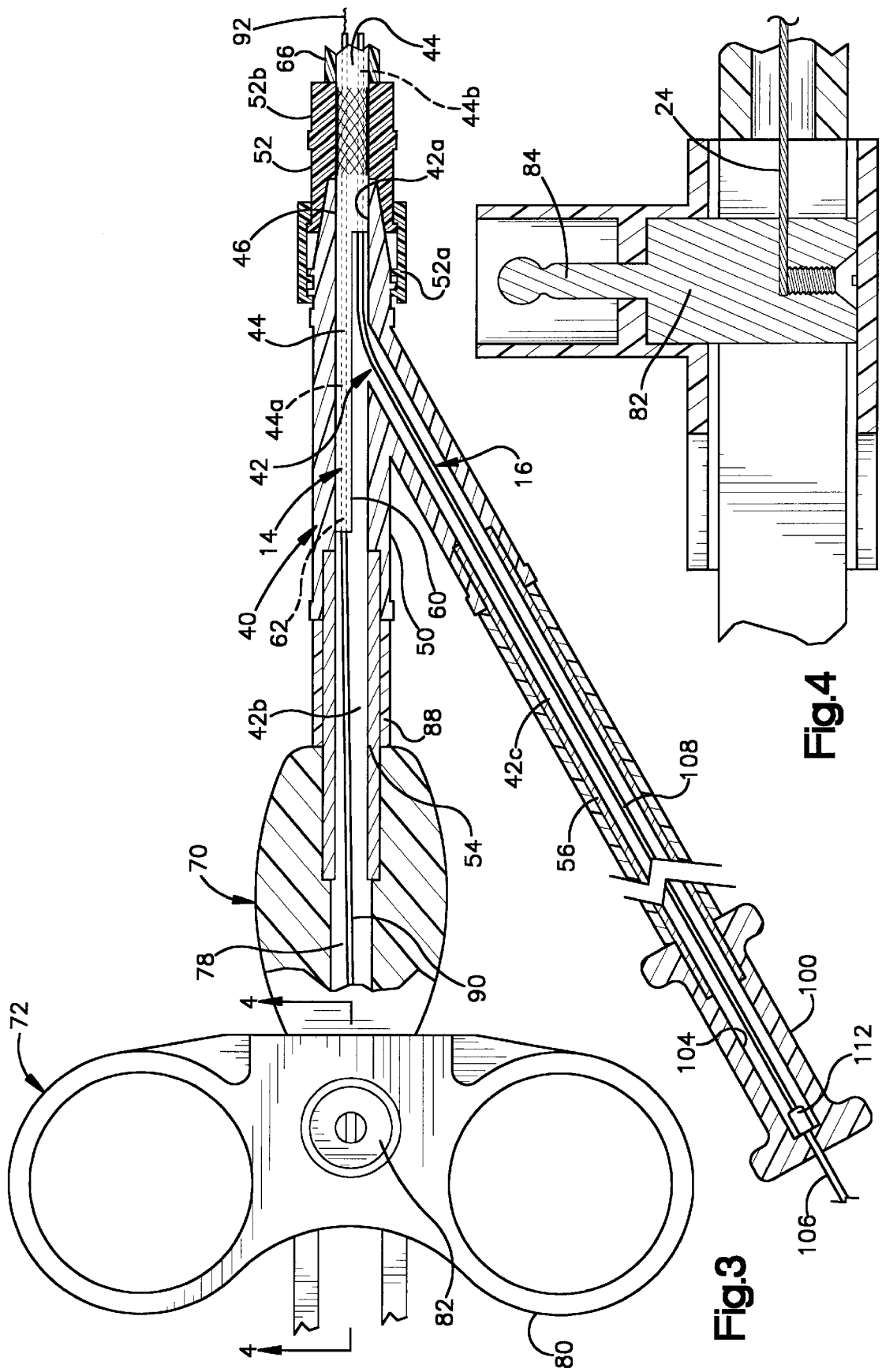

ENDOSCOPIC SURGICAL DEVICE

FIELD OF THE INVENTION

The present invention relates to surgical devices and more particularly to surgical devices constructed for removing relatively small pieces of tissue from a subject through orifices or small incisions.

BACKGROUND OF THE INVENTION

Snares and nets are in widespread use for severing and retrieving tissue from patients, or subjects. The devices are used in human and anal subjects, in laparoscopic surgeries and other procedures where access to tissue is only possible via a small opening. One exemplary use is for cutting off and retrieving intestinal polyps where a wire snare, passed through an colonoscope instrument channel, encircles and is tightened about an intestinal polyp to sever the polyp. The severed polyp is retrieved in a net inserted through the instrument channel. The net is manipulated to enclose the polyp and then withdrawn with the instrument so that the tissue architecture remains undisturbed.

In this procedure, as well as others, the net and snare must be quite compact in order to pass into the subject through the instrument channel, or other passage. Prior art proposals have employed snares supported within plastic tubes that were snaked into the subject to locate the snare where desired. The snare was then deployed from its tube, manipulated to cut off the polyp and retrieved into the tube for removal from the subject.

A net, collapsed within another tube, was introduced through the instrument channel, etc., for removing the polyp. When near a target polyp, the net was deployed, like the snare, and manipulated to net the polyp. The net was then closed sufficiently to secure the polyp and withdrawn from the subject. These proposals required use of separate snare and net devices, which in turn complicated and lengthened surgeries by increasing the number of steps required. For various reasons, devices such as the snare and net devices are constructed for disposal after a single use. Disposal of multiple devices after a single use was not cost effective.

U.S. Pat. No. 5,290,542 discloses a combined snare and net device for removing tissue from a subject. There, the snare and net were contained in a common introducer tube, commonly actuated and fastened together in tandem. The snare and net were subject to becoming ensnarled during use. Moreover, manipulating the combined snare and net was unwieldy. The proposed device was not successful.

The present invention provides a new and improved surgical device for removing tissue from a subject wherein simultaneous introduction of a snare and a net into a subject is accomplished, with the snare and net being separated and individually deployed and retrieved so that they do not interfere with each other during the procedure. Improvements in the construction and operation of both the net and the snare are also provided.

SUMMARY OF THE INVENTION

In a preferred embodiment of the invention an endoscopic surgical device for retrieving severed tissue from within a subject is provided comprising a support unit and a tissue retrieving net system. The support unit comprises a body defining a passage therethrough and an elongated introducer member having a first end section proximal and fixed with respect to the body and a second end section remote from the body, the introducer member defining a second passage aligned with the body passage and opening at the second end section.

The tissue retrieving net system is carried by the support unit and deployed from and retrieved into the introducer member for retrieving tissue. The net system comprises a net, a net deployment and retrieval assembly and a net actuator. The net comprises a wire-like resilient loop and a net element. The net element has a mouth section slidably disposed on the loop and a tissue receiving pouch section. The net is disposed adjacent the introducer member second end for deployment and retrieval through the second passage opening.

The net deployment and retrieval assembly transmits motion between the actuator and the net. The assembly extends substantially through the first and second passages and is connected to the net. The deployment and retrieval assembly comprises an elongated motion transmitting member extending in the second passage to the loop.

The net actuator comprises manually operated handles by which the net assembly is manipulated. A first handle is fixed with respect to the body and a second handle is fixed with respect to the motion transmitting member and movable relative to the first handle. Shifting the second handle relative to the first handle shifts the net into and out of the second passage opening.

The introducer member and the net cooperate so that the net is collapsed when retrieved into the introducer member. The introducer member passage has a diametrical extent substantially smaller than the width of the net loop. The introducer member engages the loop at the second end section opening and resiliently collapses and elongates the loop as the net is retrieved and moves into the introducer member passage. The loop resiliently returns to its uncollapsed configuration as it is deployed.

The net system further comprises a net controller for assuring that the net mouth extends fully about the loop when the loop is deployed. The controller comprises an anchor fixed within the introducer member passage and a tether fixed to the anchor and to the net. The anchor is located a distance from the second passage opening equal to at least half the length of the loop in its collapsed condition. The net tether has one end fixed to the anchor, an opposite end secured to the net mouth and a free length equal to the aforesaid distance. The tether assures full net mouth opening when the net is deployed while permitting the mouth to be closed when tissue is disposed in the net body and the loop is retrieved.

The preferred device further comprises a tissue severing snare system comprising a snare, a snare actuator unit, and a snare deployment and retrieval assembly between the actuator unit and the snare for transmitting motion to the snare. The introducer supports the net and the snare adjacent the second end section and supports at least part of each deployment and retrieval assembly. The deployment and retrieval assemblies coextend through the introducer. The introducer member defines first and second lumens at the second end section with the snare and net each deployed and retrieved through a respective lumen.

In a preferred and illustrated embodiment the support unit body defines a bifurcated passage with the net actuator and the snare actuator located at the ends of respective passage bifurcations remote from their juncture and the retrieval and deployment assemblies coextending from the trunk body unit passage into the introducer. The support unit and the retrieval and deployment assembly of one of the snare and net systems are so constructed and arranged that deployment and retrieval motion is transmitted through an angle between the associated passage bifurcation and the trunk passage.

Further features and advantages of the invention will become apparent from the following detailed description of a preferred embodiment made with reference to the accompanying drawings.

BRIEF DESCRIPTION OF THE DRAWINGS

FIG. 1 is an elevational view, shown partly in cross section, of a surgical device constructed according to the present invention;

FIG. 2 is a view similar to FIG. 1 with parts illustrated in alternative positions;

FIG. 3 is an enlarged fragmentary view of part of the device illustrated in FIG. 1;

FIG. 4 is a view seen approximately from the plane indicated by the line 4—4 in FIG. 3;

FIG. 6 is a view seen approximately from the plane indicated by the line 6—6 in FIG. 5 and shown on a scale that is larger than the scale of FIG. 5;

BEST MODE CONTEMPLATED FOR CARRYING OUT THE INVENTION

Figure 5:
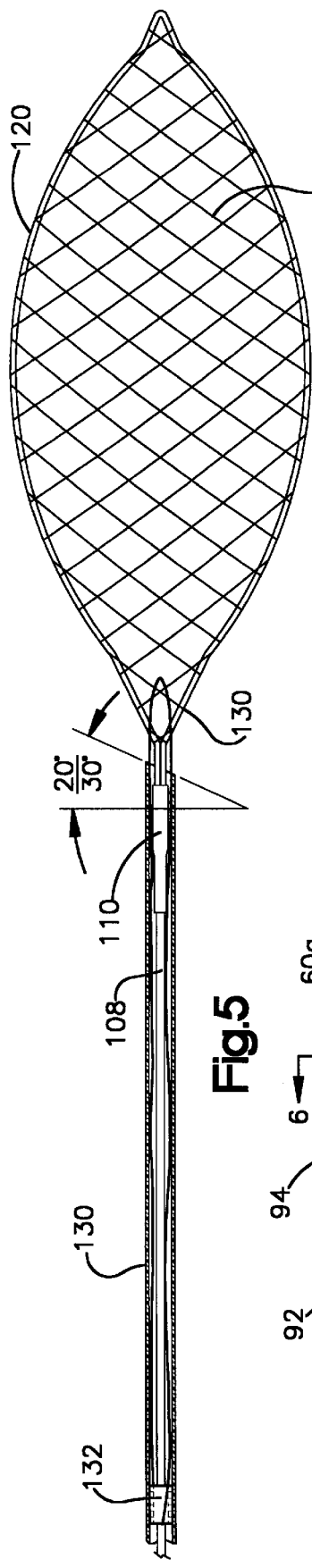
FIG. 5 is an enlarged fragmentary view of part of the device illustrated in FIG. 2.

An endoscopic surgical device 10 for severing tissue within a subject and for retrieving severed tissue from within the subject is illustrated by the drawings. Referring to FIGS. 1 and 2 the device 10 comprises a support unit 12, a tissue severing snare system 14, and a tissue retrieving net system 16. The snare and net systems are carried by the unit 12 and are so constructed and arranged that they may be inserted into the subject through an orifice or small incision and individually operated to sever and retrieve tissue. Accordingly, the snare system 14 comprises a snare 20, a snare actuator 22, and a snare deployment and retrieval assembly 24 for transmitting motion between the actuator and the snare. Similarly, the net system 16 comprises a net 26, a net actuator 28, a net deployment and retrieval assembly 30 for transmitting motion between the net and its actuator 28, and a net controller 32 for assuring the net is fully opened when deployed. The device 10 can be used with any suitable or conventional laparascopic surgical equipment. For purposes of this disclosure the device 10 is described in the context of use with an endoscope/colonoscope/sigmoidoscope type apparatus (not illustrated), of conventional or suitable construction. The scope is provided with an elongated body having a controllably flexible projecting end region. Surgical instruments, such as the device 10, may be introduced through an instrument channel, which extends through the scope body, for excising and removing tissue targeted by the surgeon manipulating the scope.

The support unit 12 supports the snare and net systems so that the net 26 and snare 20 can be inserted through the scope instrument channel while the respective actuators are supported accessible to the surgeon. The support unit 12 comprises a body 40 defining a passage 42 therethrough (FIG. 3) and an elongated introducer 44 having a first end section 46 proximal and fixed with respect to the body 40 and a second end section 48 remote from the body. The introducer 44 is tubular and aligned with the body passage 42 for receiving the net and snare systems.

The body 40 is constructed and arranged so that the snare and net assemblies are independently operable by the surgeon without interfering or clashing with each other. The illustrated body 40 is constructed so that the passage 42 is bifurcated, providing a trunk section 42a and branches 42b, 42c diverging from each other. The snare system 14 extends through the trunk and branch 42b while the net system 16 extends through the trunk and branch 42c. In the preferred construction the trunk and branch 42b are aligned so the snare system extends in a straight line through the body 40. The branch 42c extends from the trunk at an obtuse angle so the net system 16 makes a turn as it extends through the body 40.

The illustrated body 40 is a rigid, tubular Y-shaped member formed by a Y-shaped molded plastic base 50, a luer 52 extending about the base trunk section, and rigid branch members 54, 56 projecting from the base Y arms. The branch members 54, 56 are each formed by a length of hypodermic needle tube stock extending into a respective base Y arm and securely bonded in place.

The preferred and illustrated introducer 44 is a smooth, supple member capable of being snaked through the scope instrument channel into the subject and readily flexed into any shape required as the scope body is flexed by the surgeon. The introducer 44 is a dual lumen element in that at least the net and the snare are housed in separate passages 44a, 44b within the introducer, thus avoiding clashes between the net and snare systems that could otherwise occur. See FIGS. 3 et seq. In the illustrated and preferred embodiment the introducer is a generally cylindrical, small diameter tube formed of nonreactive low friction plastic material, such as polytetrafluouroethylene. The first end section 46 is fixed to the base 50 via the luer 52 while the second end section 48 houses the snare and the net for individual deployment and retrieval. The second end section 48 is provided with a thin septum 60 extending across the interior of the introducer to define two D-shaped lumens 62, 64 each surrounding a respective snare and net and through which the respective associated snare or net is deployed and retrieved. See FIG. 6. The longitudinal central septum portion 60a is slightly crowned at least in the region close to the introducer end opening. The preferred introducer is extruded so the septum 60 extends continuously between the ends of the introducer. While the introducer is illustrated as a cylindrical tube containing a septum, it could take other forms defining dual lumens.

The introducer is fixed to the body 40 so that the lumen 62 receives the snare deployment and retrieval assembly and the lumen 64 receives the net deployment and retrieval assembly. The introducer end section 46 is fixed to the body 40 by the luer 52. The luer comprises a first annular element 52a fixed about the base trunk (for example, by press fitting) and a second element 52b fixed to the introducer 40 (for example, by etching the introducer and bonding it to the element 52b). The element 52a is formed with internal threads and the element 52b is threaded so the elements can be screwed together. A flexible strain relief band 66 is secured tightly about the introducer adjacent the luer element 52b to prevent the introducer from being bent too abruptly near the body 40.

The introducer end section 46 extends through the element 52b into the body 40 where it terminates in the passage branch 42b. The cylindrical wall of the introducer end section 46 is cut away so that the lumen 62 extends into the passage 42b. The introducer wall is cut back to the point where the lumen 64 is disposed adjacent the passage branch 42c for receiving the net deployment and retrieval assembly. The septum 60 thus extends between the deployment and retrieval assemblies throughout the length of the introducer in which they coextend.

The snare actuator 22 is supported at the end of the branch member 54 for reciprocating the deployment and retrieval assembly in the body and introducer to operate the snare 20. The actuator 22 comprises a first handle 70 fixed with respect to the body 40 and a second handle 72 attached to the deployment and retrieval assembly 24 and movable with respect to the handle 70.

The illustrated handle 70 is defined by an elongated body having an enlarged end 74 receiving and bonded to the tubular branch member 54, a thumb ring 76 at its opposite end, a longitudinal slot 77 extending in the body between the ends and a bore 78 extending through the end 74 to the branch passage 42b. The deployment and retrieval assembly 24 extends through the bore 78 for connection to the handle 72.

The second handle 72 is fixed to the assembly 24 and mounted on the handle 70 between its ends for longitudinal sliding movement. The second handle comprises a dual finger ring member 80 slidable on the handle 70 and a connector pin 82 fixed at both ends to the finger ring member and extending transversely through the slot 77. The connector pin 82 is joined to the assembly 24 in the slot 77 at a location aligned with the bore 78 so that the assembly 24 reciprocates relatively freely in the bore when the member 80 moves back and forth along the handle 70. The connector pin engages the opposite slot ends to limit the second handle travel and thereby limit the snare travel.

The illustrated snare system simultaneously cuts and cauterizes tissue. Accordingly, the snare 20, as illustrated, is electrically resistance heated by a circuit completed from a suitable R.F. power supply (not shown) through the connector pin 82, the assembly 24, the snare 20 and the subject's body (which is suitably grounded). The illustrated connector pin 82 comprises a conductive brass body mechanically fixed in the finger ring member 80, electrically connected to the assembly 24 and detachably connectable to the power supply. The connector pin receives the end of the assembly 24 in a drilled hole aligned with the bore 78. The assembly end is mechanically and electrically connected to the connector by a set screw in a tapped cross drilled hole in the connector. The terminal post 84 projects from an end of the connector pin within a cylindrical insulative collar forming part of the ring member 80.

The handles 70, 72 are preferably formed from molded plastic electrically insulating materials, except for the connector pin 82. The exposed portion of the member 54 is surrounded by a tube 88 of insulative material to insure against the possibility of electrical shocks or burns from incidental contact. The septum 60 electrically isolates the snare deployment and retrieval assembly from the net deployment and retrieval assembly. The terminal post 84 plugs to a female power supply connector. Electrical power is supplied to the snare from the power supply via an on-off switch, which is of any conventional or suitable construction and therefore not illustrated, controlled by the surgeon.

While a snare heating circuit completed through the subject's body is illustrated, the device 10 may as well be constructed as a so-called bipolar device with the heater circuit completed through the snare system across power supply terminals.

Figure 7:
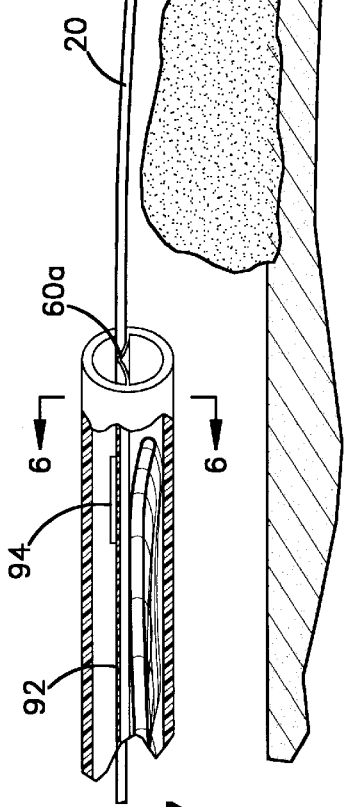
FIG. 7 is a fragmentary cross sectional view seen approximately from the plane indicated by the line 7—7 in FIG. 6.

The deployment and retrieval assembly 24 is constructed and arranged to transmit considerable deployment and retractive forces to the snare while enabling the scope body to be freely manipulated and flexed to position the snare where desired. The assembly 24 comprises a first link 90 connected to the actuator 22 for transmitting compressive and tensile forces between the handle 72 and the bore 78, a second link 92 for transmitting forces through the introducer 44, and a snare connector 94 (FIG. 7). The illustrated link 90 is a relatively rigid rod-like structure extending unsupported along the slot 77. The link 90 transmits relatively substantial compressive forces across the length of the slot 77 without bending or breaking. The link 90 is preferably formed from hypodermic needle stock, i.e. it is a cylindrical stainless steel tube.

The link 92 extends within the body 40 and the introducer 44 so that it must flex with the introducer yet transmit compressive and tensile forces. The illustrated link 92 is formed by a thin, relatively stiff, yet flexible, wire closely surrounded by the body passage 42b and the introducer passage 44a (lumen 62). The wire is relatively stiff compared to the supple introducer. When transmitting compressive forces, the link wire is resiliently deformed to bow against the introducer wall. The lumen 62 closely surrounds the wire with the introducer passage wall constraining the wire against bending or kinking so the wire exhibits considerable strength in compression. In the illustrated embodiment the wire is a thin multi-strand cable-like stainless steel structure.

The link 92 is telescoped into the open end of the link 90 at least to a location adjacent the connector pin where the link 90 is crimped against the link 92 and the two are resistance welded together to assure a structurally strong electrically conductive joint.

The connector 94 joins the link 92 and the loop 20 together both structurally and electrically. The illustrated connector 94 is a short tube crimped and welded to both the snare 20 and to the link 92. The preferred connector tube is crimped about the snare and link to form a "D" shaped, or elliptical, cross sectional shape (see FIG. 6), which is not capable of rotating within the lumen 62. The connector tube thus maintains the snare loop in a plane generally parallel to the septum 60. The preferred connector is formed from hypodermic needle stock, like the link 90.

The snare 20 is formed from a loop of fine wire constructed and arranged to cooperate with the introducer to sever tissue by a combination of cutting and cautery in an extremely effective manner. The illustrated snare 20 is a stiffly resilient, flexible conductive wire having its ends crimped in place and welded together by the connector 94. When the snare is deployed from the end of the introducer, the loop resiliently expands to a relaxed condition where the loop width is substantially greater than the introducer diameter. The deployed snare is guided to a position where it encircles a target polyp or other tissue. The on-off control switch, not illustrated, is closed to heat the snare. The snare is retracted by the surgeon. As the snare is retracted into the introducer lumen 62 the snare loop resiliently bears against the introducer wall so the snare resiliently collapses, narrowing the snare loop portion projecting from the introducer. Tissue encircled by the projecting snare loop portion is progressively constricted by the relatively fine loop wire while being drawn to the end of the introducer. The introducer end is cut on an angle of 20–30 degrees from a plane normal facilitate snaking the introducer through the instrument channel.

The preferred snare 20 is crimped in several places before it is formed into a loop to further enhance its tissue severing effectiveness. The projecting loop portion is crimped at three locations 20a–c to form a "V" shaped loop projection at the loop extremity. Two additional loop crimps 20d–e near the distal side of the loop provide for a smaller loop width than would otherwise obtain and ease the loop retraction.

Figure 8:
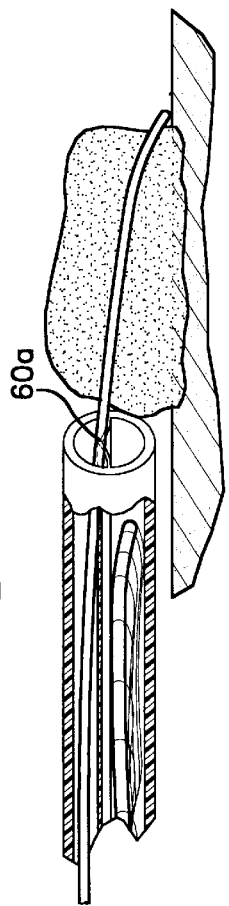
FIG. 8 is a view like FIG. 7 with parts illustrated in an alternative position.
Figure 9:
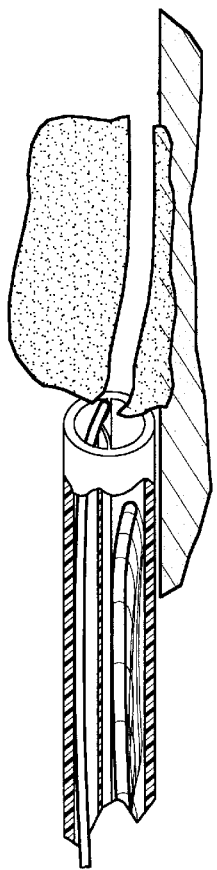
FIG. 9 is a view like FIG. 7 with parts illustrated in an alternative position; and, FIG. 10 is a perspective view of a part of the device.

The snare loop resiliently engages the introducer wall as the snare retracts, thus forcing the wall engaging loop sections toward the maximum diametrical width of the introducer, i.e. where the edges of the septum wall join the cylindrical introducer wall. The snare loop is constrained toward lying in a the plane of the wall engaging loop sections as the loop is drawn into the introducer. The septum crown portion 60a projects through the loop plane so the "V" loop snare portion is drawn toward and across the septum crown as the snare is retrieved. This operation is illustrated in FIGS. 7–9. As the "V" loop portion enters the introducer, the tissue within it is sliced by the thin, angled septum wall and nipped off by the septum crown as is engages the "V" loop tip entering the lumen.

The net system actuator 28 is stationed at the projecting end of the body branch member 56 for reciprocating the net 26 between its deployed and retrieved positions. The actuator 22 comprises a first handle 100 fixed with respect to the body 40 and a second handle 102 attached to the deployment and retrieval assembly 30 and movable with respect to the handle 100.

The handle 100 is defined by a body having socket-like opening receiving and bonded to an end of the branch member 56 and a bore 104 extending through the handle body through which part of the net deployment and retrieval assembly 30 extends from the branch member to the second handle member 102. In the illustrated device the handle body is a molded plastic element formed like a spool with a generally cylindrical, central body sized to be gripped between index and fore fingers and opposite axial flanges to prevent loss of grip. A plastic tube 105 like the tube 88) surrounds the branch member 56 and extends between the handle 100 and the body 40.

The handle 102 is fixed to an end of the deployment and retrieval assembly 30 for shifting the assembly back and forth through the handle bore 104. The illustrated handle 102 is formed by a molded plastic thumb ring having a projecting element fixed to the assembly 30.

The net loop deployment and retrieval assembly 30 transmits compressive and tensile forces from the actuator 28 to the net 26 for deploying and retrieving the net. The assembly comprises a first link 106 connected to the handle 102 and extending through the bore 104 into the branch member 56, a second link 108 extending between the link 106 and the net, and a connector 110. The illustrated link 106 extends unsupported from the handle 100 to the handle 102 and accordingly is formed by a relatively rigid rod-like element that can transmit compressive forces without bending. The rigid nature of the link 106 precludes the link from bending appreciably without yielding and kinking. In the preferred device the link 106 is formed from stainless steel hypodermic needle tube stock, which has good compressive and tensile strength and is somewhat resiliently bendable, but can not be trained around the obtuse angle corner formed by the trunk passage 42a and the branch passage 42c.

The link 108 extends in the body 40 around the obtuse angle corner between the branch passages 42a, 42c and into the introducer 44 so that it must flex yet transmit compressive and tensile forces. The illustrated link 108 is formed by a thin, relatively stiff, yet flexible, wire. The wire is closely surrounded by the branch member 56, the passages 42c, 42a and the introducer passage 44b. The wire is relatively stiff compared to the supple introducer. When transmitting compressive forces the link wire is resiliently deformed to bow against the adjacent walls of the body 40 and the introducer wall. The body walls and the lumen 64 closely surround the wire and constrain it against bending or kinking so the wire exhibits considerable strength in compression. The preferred wire is a thin multi-strand stainless steel cable.

The link 108 is telescoped into the open end of the link 106. The link 106 is crimped against the link 108 and the two are welded together.

An important aspect of the device 10 design resides in the constructions of the branch member 56 and the link 106 which assure that the projecting end of the link 106 can not be forced around the corner between the passages 42c, 42a and that the flexible link 108 can not be withdrawn through the bore 104. The length of the branch member 56 is selected so that when the handle 102 engages the handle 100 (the travel limit of the link 106 with the net fully deployed), the projecting end of the link 106 is spaced from the juncture of the passages 42a, 42c. The link 106 is stamped to provide a flattened, travel limiting stop 112 adjacent its projecting end. See FIG. 3. The stop 112 has a larger diametrical extent than the bore 104 so the stop engages the handle 100 when the handle 102 has been moved away from the handle 100 sufficiently to fully retrieve the net into the lumen 64. The travel limitation assures the link 108 is not pulled through the bore 104.

The net connector 110 joins the link 108 and the net 26. The illustrated connector 110 is "D" shaped, or elliptical, in cross section like the connector 94 (FIG. 6) so that the net can not rotate about the axis of the link 108 in the lumen 64. The connector 110 is crimped and welded to both the net and the link 108. The preferred connector is formed from hypodermic needle stock, like the connector 94.

The net 26 is deployed from the introducer lumen 64 and manipulated by the surgeon to net severed tissue and secure the tissue for retrieval from the subject. The net 26 is preferably deployed after the snare has severed the target tissue and been retrieved into the introducer 44. This avoids interference or clashing of the net and snare systems and simplifies net manipulation. The net 26 comprises a stiffly resilient loop 120 and a pouch-like net element 122 slidably supported on the loop 120.

The preferred net loop 120 is constructed identically to the snare 26. The net loop 120 is not described in further detail for the sake of brevity. Reference should be made to the foregoing snare description for an understanding of constructional details.

The net element 122 is an extremely light pouch-like structure having the net loop wire extending through the mesh about its periphery to form a net mouth slidably supported on the loop and a depending pouch. The net fibers are quite fine, yet sufficiently strong that the net element may slide along the loop wire in the direction away from the connector 110 to enclose tissue within the pouch as the net is retrieved and/or to gather the entire net at the distal net loop end when the net loop has been retrieved. The net has minimal bulk so that when an empty net is retrieved, the net easily moves completely into the introducer passage 44b whether the net is gathered at the distal loop end or remains distributed along the net loop periphery. The ease of retrieval into the introducer passage 44b is enhanced by the septum crown construction projecting away from the net to increase the area of the lumen 64.

The illustrated and preferred net is formed from 100% nylon fibers having strand diameters of from about 0.0125 mm–0.04 mm. The fibers are woven in a diamond mesh pattern with the mesh strands spaced from 1–3 mm and their intersections fixedly secured together. The preferred netting material is substantially like that of a fine mesh hair net. The net is formed by cutting about a square, circular or elliptical section of the net, trimming or otherwise finishing the edges and threading the loop wire through the peripheral mesh elements. The cut net section size is selected sufficiently larger than the net loop area to assure that a pouch-like, tissue receiving portion depends from the net mouth.

Attempting to fully retrieve a tissue containing net into the introducer 44 can result in tissue loss by forcing the tissue through the net. The net fibers are fine and strong so they may cut the tissue or they may be broken, either of which alternative is undesirable. The net actuator thumb ring 102 may be provided with a tag (not illustrated) warning the surgeon not to continue retrieving the net against unusual resistance.

The net controller 32 assures that the net periphery is automatically distributed fully and evenly around the net loop when the net has been fully deployed. The preferred controller comprises a net tether 130 anchored in the introducer passage at a location spaced from the introducer end at least one half the maximum distance between the net loop projecting end and the net connector 110 (the net length), but preferably two to three times the net length. The preferred tether 130 is a limp, string-like member formed in a loop threaded through two or three net fibers along the net periphery located nearest the net connector 110. The preferred tether is formed from suture thread. The tether 130 is taut when the net is fully deployed and the mouth evenly distributed about the net loop. When the net is retrieved the tether 130 is carried further into the introducer passage 44b by the link 108 with which the tether is frictionally engaged. The frictional engagement tends to assure the net 26, when retrieved empty, remains evenly distributed on the net loop even as the net loop is pulled into and frictionally engaged and collapsed along the introducer channel 44b.

In the illustrated embodiment of the invention the tether is anchored in the passage 44b by an anchor element 132 inserted in the passage and firmly engaging the introducer wall to resist withdrawal. The tether 130 is looped around the anchor and thus firmly held in place. While the anchor could take any suitable form, the illustrated anchor element is formed from a short, semicylindrical piece of stamped stainless steel sheet having barb-like teeth formed along its opposite edges. The element, with the tether loop disposed about its axial extent, is forced into passage 44b to the desired location spaced from the introducer end. The tether 130 is then threaded through the net fibers and tied to complete the tether loop. The barb teeth on the anchor dig into the introducer wall material to prevent dislodging the anchor once positioned where desired. The anchor can also be formed by a short cylindrical tube of stainless steel, or equivalent metal, having an array of annular barb teeth extending about its periphery.

While a single embodiment of the invention has been illustrated and described in considerable detail, the present invention is not to be considered limited to the precise construction disclosed. Various adaptations, modifications and uses of the invention may occur to those skilled in the arts to which the invention relates. It is the intention to cover all such adaptations, modifications and uses falling within the scope or spirit of the annexed claims.

Having described my invention I claim:

1. An endoscopic surgical device for retrieving severed tissue from within a patient's body, the device comprising:
   a. a support unit comprising:
      i. a body defining a passage therethrough; and
      ii. an elongated introducer member having a first end section proximal and fixed with respect to said body and a second end section remote from the body, the introducer member defining a passage aligned with the body passage and opening at said second end section; and,
   b. a tissue retrieving net system comprising:
      i. a net comprising a wire-like resilient loop and a net element having a mouth section slidably disposed on the loop and a tissue receiving pouch section, said net disposed adjacent said second end for deployment and retrieval through said introducer passage opening;
      ii. a net deployment and retrieval assembly extending substantially through said introducer passage and connected to the net, said assembly comprising a motion transmitting member extending in said introducer passage to said loop; and,
      iii. a net actuator unit comprising a first handle fixed with respect to said body and a second handle fixed with respect to said motion transmitting member and movable relative to said first handle so that shifting the second handle relative to said first handle shifts said net into and out of said introducer passage opening;
   c. said introducer member passage having a diametrical extent substantially smaller than the width of said loop when said loop is deployed, said introducer member engaging said loop at said opening and resiliently collapsing and elongating said loop as said net is retrieved and moves into said introducer member passage, said loop resiliently returning to an uncollapsed configuration as an is deployed;
   d. said net system further comprising a net controller for assuring that said net mouth extends fully about said loop when said loop is deployed, said controller comprising a net tether having one end anchored within said introducer member passage a distance from said second introducer member end section equal to at least half the length of said loop in an collapsed condition, an opposite end secured to said net mouth, and a free length equal to said distance, said tether assuring full net mouth opening when the net is deployed while permitting said mouth to be closed when tissue is disposed in said net pouch and the loop is retrieved.

2. The surgical device claimed in claim 1 further including an anchor to which said net tether is secured, said anchor extending at least part way about the interior of said introducer passage in tight engagement with said introducer member and part of said tissue retrieving net system extends within said introducer passage past said anchor.

3. An endoscopic surgical device for severing tissue within a subject and for retrieving severed tissue from within the subject, the device comprising:
   a. a tissue severing snare system comprising a snare, a snare actuator unit, and a snare deployment and retrieval assembly between the actuator unit and the snare for transmitting motion to the snare;
   b. a tissue retrieving net system comprising a net comprised of a wire-like loop and a pouch-like net element slidably disposed on the loop, a net loop actuator unit, and a net loop deployment and retrieval assembly between the net loop and the net loop actuator unit for transmitting motion to the net; and, c. a support unit for the systems comprising a body for supporting each of said actuator units and a snare and net introducer having a first end section proximal and fixed with respect to said body and a second end section operable to position said net and snare at desired locations remote from said body;

d. the introducer supporting said net and snare adjacent said second end section and supporting at least part of each deployment and retrieval assembly, said deployment and retrieval assemblies coextending through said introducer, said introducer member defining first and second lumens at said second end section with said snare and net each deployed and retrieved through a respective lumen;

e. each deployment and retrieval assembly comprising a thin, flexible wire-like motion transmitting member between its associated actuator unit and its associated net or snare, said motion transmitting member extending within an introducer guide passage that closely surrounds said motion transmitting member and constrains said member for translational longitudinally motion within said passage;

f. each deployment and retrieval assembly further comprising a connector between said motion transmitting member and its associated net or snare, said connector shaped to preclude rotation of the motion transmitting member and associated net or snare in said introducer.

4. An endoscopic surgical device for retrieving severed tissue from within a patient's body, the device comprising:

a. a support unit comprising:
 1. a body defining a passage therethrough; and
 2. an elongated introducer member having a first end section proximal and fixed with respect to said body and a second end section remote from the body, the introducer member defining a passage aligned with the body passage and opening at said second end section; and, b. a tissue retrieving net system comprising:
 1. a net comprising a wire-like resilient loop and a net element, said net element having a mouth section slidably disposed on the loop and a tissue receiving pouch section, said net disposed adjacent said second end for deployment and retrieval through said passage opening; and,
 2. a net deployment and retrieval assembly extending substantially through said passage and connected to the net, said assembly comprising a motion transmitting member extending in said passage to said loop;

c. said introducer member passage having a diametrical extent substantially smaller than the width of said loop when said loop is deployed, said introducer member engaging said loop at said second end section opening and resiliently collapsing and elongating said loop as said net is retrieved and moves into said introducer member passage, said loop resiliently returning to an uncollapsed configuration as it is deployed;

d. said net system further comprising a net controller for assuring that said net mouth extends fully about said loop when said loop is deployed, said controller comprising a net tether having one end fixed within said introducer member passage proximal to said introducer member end section opening and an opposite end secured to said net mouth, and a free length at least equal to the distance between said fixed end and said introducer end section opening.

5. The surgical device claimed in claim 4 further comprising an anchor to which said one end of said net tether is secured, and wherein said anchor extends at least part way about the interior of said passage in tight engagement with said introducer member and part of said tissue retrieving net system extends within said passage past said anchor.

* * * * *